(12) United States Patent
Cuillery et al.

(10) Patent No.: US 7,749,986 B2
(45) Date of Patent: Jul. 6, 2010

(54) HOMOGENEOUSLY FORMULATING MICRODOSED ACTIVE PRINCIPLES

(75) Inventors: Yves Cuillery, La Balme de Silligny (FR); Denis Chambinaud, Chambery (FR)

(73) Assignee: Galderma S.A., Cham (CH)

( * ) Notice: Subject to any disclaimer, the term of this patent is extended or adjusted under 35 U.S.C. 154(b) by 236 days.

(21) Appl. No.: 11/797,634

(22) Filed: May 4, 2007

(65) Prior Publication Data

US 2007/0249570 A1 Oct. 25, 2007

Related U.S. Application Data

(60) Division of application No. 11/269,854, filed on Nov. 9, 2005, now abandoned, which is a continuation of application No. PCT/FR2004/001116, filed on May 7, 2004.

(30) Foreign Application Priority Data

May 12, 2003 (FR) .................................. 03 05684

(51) Int. Cl.
*A61K 31/59* (2006.01)
*A61K 9/06* (2006.01)
*A61K 9/50* (2006.01)

(52) U.S. Cl. ........................ 514/167; 424/400; 424/484

(58) Field of Classification Search .................. 514/167
See application file for complete search history.

(56) References Cited

U.S. PATENT DOCUMENTS

| | | | | |
|---|---|---|---|---|
| 4,380,534 A | * | 4/1983 | Fukui et al. | 424/498 |
| 4,407,824 A | * | 10/1983 | Eckert | 514/555 |
| 4,761,407 A | | 8/1988 | Campan et al. | |
| 5,834,016 A | * | 11/1998 | Naeff et al. | 424/450 |
| 2002/0010164 A1 | | 1/2002 | Abrahamson et al. | |

OTHER PUBLICATIONS

Remington's Pharmaceutical Sciences. 18th edition. p. 1477-1478 and 1606 (1990).*

* cited by examiner

*Primary Examiner*—Jake M. Vu
(74) *Attorney, Agent, or Firm*—Buchanan Ingersoll & Rooney PC

(57) ABSTRACT

A microdose of at least one active principle is homogeneously formulated as an ointment using a container with perforations having a size and shape that permit diffusion of the active principle(s) and petroleum jelly through the perforations, by: (a) weighing the at least one active principle in a container lined with a petroleum jelly; (b) encapsulating the active principle with additional petroleum jelly; (c) introducing the container with the active principle(s) and the petroleum jelly into a mixer, where the mixer contains at least one excipient in a heated liquid state; and (d) immersing the container within the at least one excipient in a heated liquid state, thereby melting the petroleum jelly, which causes diffusion of the active principal(s) and the melted petroleum jelly and microdoses the active principle(s) in the excipients.

11 Claims, 2 Drawing Sheets

HOMOGENEOUSLY FORMULATING MICRODOSED ACTIVE PRINCIPLES

CROSS-REFERENCE TO PRIORITY/PCT APPLICATIONS

This application is a divisional application of U.S. Ser. No. 11/269,854, filed Nov. 9, 2005 and claims priority under 35 U.S.C. §119 of FR 03/05684, filed May 12, 2003, and is a continuation of PCT/FR 2004/001116, filed May 7, 2004 and designating the United States (published in the French language on Nov. 25, 2004 as WO 2004/100924 A2; the title and abstract were also published in English), each hereby expressly incorporated by reference and each assigned to the assignee hereof.

BACKGROUND OF THE INVENTION

1. Technical Field of the Invention

The present invention relates to a method for preparing a pharmaceutical or cosmetic formulation, preferably an ointment, containing an active agent or a microdosed dispersible active principle.

2. Description of Background and/or Related and/or Prior Art

It is known that the manufacture of preparations with a low active principle concentration entails problems of homogenizing the active principle in its excipients. This is because microdosed active principles encounter dispersion heterogeneity problems when they are mixed with large volumes of excipients.

These preparations normally must be subjected to an intermediate dilution phase in order to obtain products with a low active principle concentration.

An additional problem arises when the active principle belongs to a class of toxic products. In this case, the handling not only takes a long time but also becomes dangerous, which significantly increases the risks of accident.

Added to this is the problem of transporting the toxic product while keeping it protected it from light and oxidation phenomena.

One example of preparations made by these methods are ointments. These are preparations for external use, intended to be topically applied directly on the skin and so must be in a predetermined range of viscosities which can be applied to the skin. If the active principle in the ointment is a solid, it will be sprinkled as finely as possible and incorporated into the ointment by the principle of geometrical dilution.

Geometrical dilution involves a series of dilution steps. It starts with the active principle being incorporated into an amount of excipient approximately of equal size. A second amount of excipient, approximately equal to the first mixture that has been formed, is added and then mixed.

This procedure with dilution steps is carried out until all of the excipient has been used, so as to obtain the intended concentration of active principle.

The various products involved in the manufacture of the ointment are generally mixed together by melting over a water bath, followed by stirring until the mixture has cooled. In this case, the active principle will be incorporated at a suitable stage. A long, drawn out iterative process is therefore required to ensure homogeneity.

SUMMARY OF THE INVENTION

A novel method for preparing a formulation containing an active principle that avoids or ameliorates the aforesaid problems of lengthy processes and risks of accidents has now been developed, comprising the following preparation steps:

1. weighing an active principle in a container lined with petroleum jelly;
2. encapsulating the active principle with additional petroleum jelly;
3. introducing the container holding the active principle and the petroleum jelly into a mixer; and
4. diffusing the active principle in the mixer.

These various steps make it possible to save time and improve quality with a view to obtaining a homogeneous product.

This is because the method according to the invention ensures a constant diffusion, in respect of the active principle diffusing from the container into the mixer, which avoids the heterogeneous dispersion observed when it is introduced "loose" into the vat of the mixer, as may have been carried out in the past.

Encapsulating the active principle in a petroleum jelly cocoon furthermore obviates the steps of diluting an active principle, and circumvents the risks of toxicity and accidents when handling the active principle after weighing, in particular while it is being transported to the vat.

Lastly, owing to the protection provided by the petroleum jelly encapsulation, the leak tightness created by the method according to the invention avoids the problems of oxidation and degradation by light.

By eliminating the intermediate dilution steps, therefore, this invention will also shorten the preparation time.

BRIEF DESCRIPTION OF THE FIGURES OF DRAWING

The invention will be described, purely by way of example, with reference to the accompanying figures of drawing, wherein.

DETAILED DESCRIPTION OF BEST MODE AND SPECIFIC/PREFERRED EMBODIMENTS OF THE INVENTION

The present invention features a method for preparing a formulation, preferably an ointment, containing a microdosed active principle. Said method comprises the following preparation steps:

1. weighing an active principle in a container lined with petroleum jelly;
2. encapsulating the active principle with additional petroleum jelly;
3. introducing the container holding the active principle and the petroleum jelly into a mixer; and
4. diffusing the active principle in the mixer.

Figure 1A:
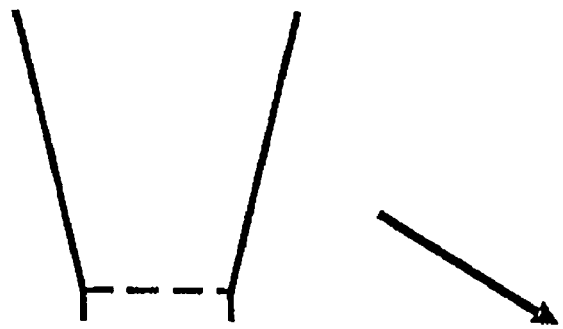
FIG. 1A shows the measuring of the weight of the container.
Figure 1B:
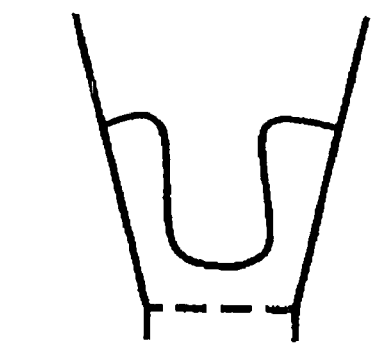
FIG. 1B shows the forming and weighing of the white petroleum jelly layer.

In particular, a homogeneous liquid formulation containing a microdosed active principle is prepared as follows:

During step 1, the weight of the container will first be measured (see FIG. 1a) before being provided with a layer of white petroleum jelly at the bottom (see FIG. 1b).

Figure 1C:
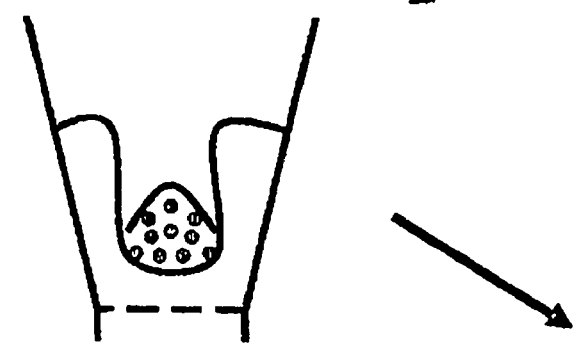
FIG. 1C shows the depositing and weighing of calcitriol.

Weighing will then be carried out in order to determine the weight of petroleum jelly which has been added. The active principle will then be introduced into the container, as indicated in FIG. 1c. The container will then be re-weighed in order to determine the exact amount of active principle which has been added.

Figure 1D:
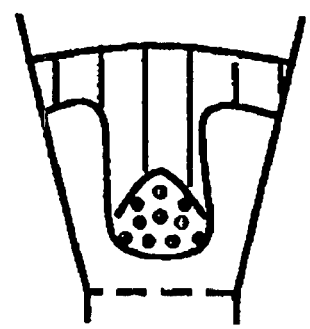
FIG. 1D shows the forming of the petroleum jelly plug.

During step 2, a plug of white petroleum jelly will be formed (See FIG. 1d) in order to encase the active principle in petroleum jelly. This intricate step needs to be carried out so as to avoid forming any air pockets which would compromise the formation of the white petroleum jelly "cocoon".

Figure 1E:
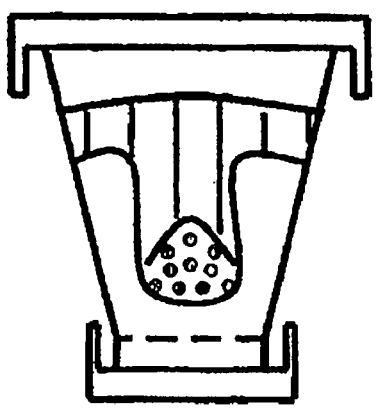
FIG. 1E shows the closing of the container with two rigid plugs.

In order to complete the preparation of the container, it will be closed by two rigid plugs (See FIG. 1e).

In this closed form of the container, the active principle encapsulated with white petroleum jelly can be transported to its processing station while being protected from light and oxidation phenomena.

Figure 3:
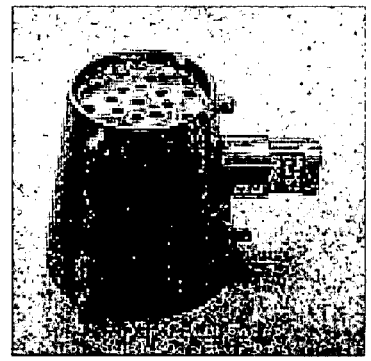
FIG. 3 shows a frusto-conical container (side view)
Figure 4:
FIG. 4 shows a perforated plug with bayonet fitting (plan view)

In order to carry out the subsequent step 3, the small plug of the container will be removed and the large plug of the container will be replaced by a perforated plug (see FIGS. 3 and 4).

Figure 6:
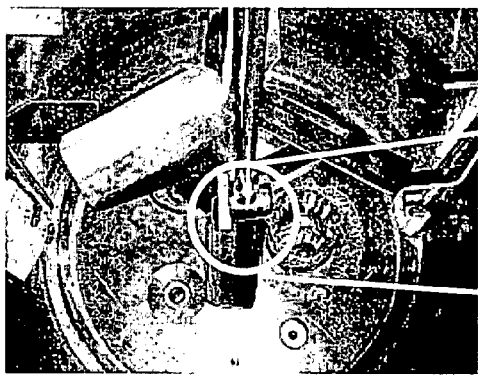
FIG. 6 shows the container fixed in the vat (plan view).
Figure 6:
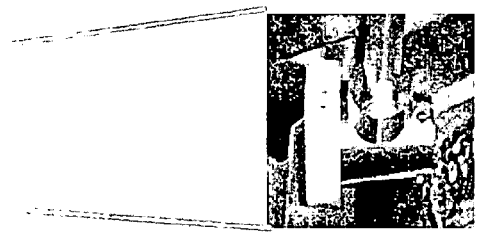

The container can thus be introduced into a vat (see FIG. 6), this vat and its excipient contents being heated sufficiently so that the mixture of excipients which it contains is in a liquid form.

During step 4, the solid petroleum jelly encapsulating the active principle will melt upon contact with the mixture of heated excipients. It will therefore be able to diffuse and be distributed homogeneously among the other excipients contained in the vat of the mixer, while carrying the active principle solution with it.

This homogeneous distribution is facilitated by various factors, firstly by the temperature of the excipients in the vat, between 70° and 90° C., which therefore makes it possible to melt the petroleum jelly contained in the diffusion container holding the active principle. The homogeneous distribution is also subsequently facilitated by the grilles at the ends of the container, which only let the active principle diffuse constantly and in a small quantity. The grilles therefore prevent the formation of large masses of semisolid petroleum jelly, which would carry a large fraction of the active principle with them, leading to poor distribution and therefore to poor homogenization of the final product.

The term "microdosed active principle" means an active principle concentration of from 1 to 100 ppm, for example from 1 to 50 ppm, in particular from 1 to 10 ppm and preferably from 1 to 5 ppm.

In a preferred embodiment, the active principle used in the method according to the invention is calcitriol; in particular, it will be preferable to use calcitriol at a final concentration of 3 ppm.

The method according to the invention may of course be used to prepare compositions comprising a plurality of active agents, one or more of which are microdosed.

The term "weighing" means a taring action, or more generally a way of determining the weight or mass of a product.

In order to avoid any risk of contamination with a toxic active principle, the weighing step will preferably be carried out in a fume cupboard with vertical laminar flow or in a sealed enclosure.

In order to avoid any inaccuracy, this weighing step will preferably be carried out on a balance with an accuracy of $\frac{1}{100}$ mg.

The term "container" means any volume, receptacle or container for introducing an active principle. In the present case, the invention relates more particularly to a container of the frustoconical type.

In order to facilitate the diffusion, it is preferable to use a conic frustum whose shape will provide it with the property of facilitating and increasing the flow rate of the fluid. The flow rate will furthermore be moderated in the wide part, and this will allow better dissolving of the active principle.

The term "metal container" is preferably intended to mean a stainless steel container.

Figure 2:
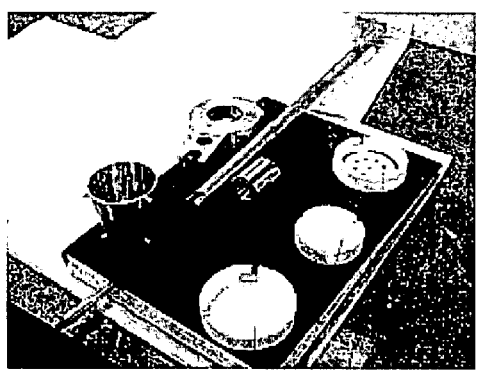
FIG. 2 shows a plan view of the various parts of the container.

In a particular embodiment of the present method, the container allowing optimal diffusion of the active principle calcitriol at a concentration of 3 ppm, in order to prepare the product Silkis, comprises the following parts (see FIG. 2):

1—a metal conic frustum (see FIG. 3) made of stainless steel, which will be covered with petroleum jelly during preparation of the formulation;

2—two solid plugs and one large perforated plug (see FIGS. 2 and 4) made of white polytetrafluoroethylene. These plugs with a bayonet system will be engaged on the container.

3—the shape of the large perforated plug (see FIG. 4) and of the grille at the small end of the container (see FIG. 3) will allow the molten petroleum jelly to diffuse when it is in contact with the hot excipient, preventing the formation of lumps.

Figure 5:
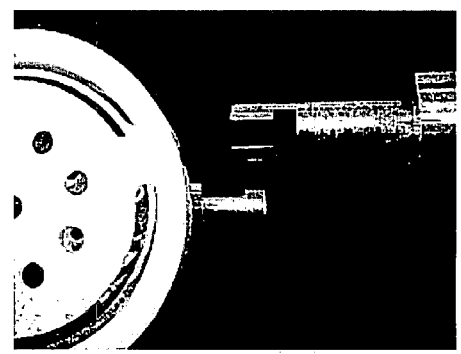
FIG. 5 shows the interlocking of the container on the rod (plan view)

The fastening of the container onto a rod with a fixed height (depending on the configuration of the vat) is carried out by interlocking as schematized in FIG. 5. In this form with a fixed height, the container will be rotatable to allow homogeneous distribution of the active principle in the vat (see FIG. 6).

The term "rigid plug" is preferably intended to mean one made of polytetrafluoroethylene or stainless steel.

The term "petroleum jelly" means any greasy substance derived from petroleum used in the composition of ointments. In this case, the invention relates more particularly to a petroleum jelly corresponding to the specifications in the European and American pharmacopoeias "Pharmeuropa" and "USP", with a viscosity of from 130,000 to 550,000 Cps.

A petroleum jelly which allows maximal limitation of the paraffin oil exudation phenomena is preferably employed.

In order to allow the formation of a hermetic assembly, this operation will preferably be carried out in a vacuum, which makes it possible to form a hermetic assembly that can be maintained for a longer time.

The term "mixture of excipients" means any mixture containing two or more excipients, for example a mixture of petroleum jelly and paraffin, in particular a mixture of from 50 to 60% white petroleum jelly and from 40 to 50% paraffin.

The term "heated" means any production of heat for raising the temperature of the excipients, such that the said excipients are in a liquid form.

Preferably, in order to allow optimum homogenization, it is important to comply with a defined temperature and homogenization time. In a preferred embodiment of the invention, for example, the temperature is from 70° to 90° C. and the homogenization time is from three hours 30 minutes to four hours 30 minutes.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1a

Weighing the Calcitriol in the Container

It is first necessary to prepare a pot and a tube of petroleum jelly, which will be used for the step of weighing the calcitriol.

The pot and the tube are weighed in the following manner:
Putting the pot and its lid on the 8 kg balance;
Reading the balance;
Taking about 50 g of petroleum jelly from the tub and introducing it into the pot;
Re-closing the pot and re-zeroing the balance;
Putting the tube on the balance;
Reading the balance;
Taking about 50 g of petroleum jelly from the tub and introducing it into the tube; and
Closing the tube using the folding mechanism.

After this phase of preparing the petroleum jelly, the conic frustum is prepared with the petroleum jelly in the following manner:

It will first be necessary to place the stainless steel conic frustum, with its solid lower plug and its solid upper plug fitted, on the plate of the balance, then the balance is read before filling the container with petroleum jelly using a spatula. The conic frustum should be ⅔ full and have a depression at its center, where the calcitriol will be introduced. The mass of petroleum jelly added will then be noted before introducing the said conic frustum of petroleum jelly into the sealed enclosure.

The phial of calcitriol is introduced into the sealed enclosure beforehand, such that it is at the same temperature as the compartment when it is weighed.

The calcitriol introduced into the conic frustum will then be differentially weighed. This step of introducing the calcitriol is carried out by progressive pouring, to avoid scattering the powder.

After this step of weighing the active principle, the depression containing the calcitriol will be covered with the petroleum jelly contained in the tube.

The conic frustum formed in this way will be covered using the two solid plugs with a bayonet fitting, and can be transported to its processing station while being protected from any risk of toxicity.

Example 1b

Manufacture of the Product Silkis 3 ppm 1a) the manufacturing vat is filled with white petroleum jelly such that it constitutes 56.2487% of the final formulation. This petroleum jelly is firstly pre-melted at a temperature allowing it to enter a liquid state, then heated in nitrogen and while stirring under temperature conditions for maintaining this petroleum jelly in the liquid and homogeneous state.

1b) In parallel, a kettle is filled with liquid paraffin so that it constitutes 43.75% of the final formulation. It is then heated in nitrogen and while stirring to a temperature equivalent to that used for the petroleum jelly in step 1a).

1c) The active principle will also be prepared in a sealed enclosure during this first step. To that end, the calcitriol will be weighed in a petroleum jelly cocoon, under inactinic light and in nitrogen, such that the calcitriol constitutes 0.0003% of the final formulation.

2) After these three compounds have been prepared, the hot paraffin is firstly introduced into the vat containing the petroleum jelly.

3) D.L. alpha tocopherol is then added to this mixture of excipients, in a concentration such that it constitutes 0.001% of the final formulation.

4) This mixture of the three excipients will then be degassed and maintained in nitrogen.

5) This is followed by a homogenization phase, during which stirring is continued in a vacuum.

6) After this homogenization step, the conic frustum containing the calcitriol will be introduced under inactinic light into the vat containing the three excipients.

7) Following this step, degassing and re-inerting with nitrogen will be carried out in a vacuum.

8) This assembly will then subjected to the time necessary for homogenization in a vacuum.

9) After this latter homogenization phase, the formulation will be allowed to cool in a vacuum in order to avoid any inclusion of air in the mixture.

10) The final step will be primary packaging in the liquid state in nitrogen, with slow stirring and under inactinic light.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for essentially homogeneously formulating as an ointment a microdose of at least one active principle within at least one excipient therefor utilizing a container having an inner surface, an open top and a perforated bottom, wherein said perforated bottom comprises a plurality of perforations having a size and shape as to permit diffusion of a molten mixture of said active principle(s) and petroleum jelly through said perforations, comprising the following steps:

(a) weighing said at least one active principle contained in said container, wherein said container contains a layer of a petroleum jelly, wherein said layer of petroleum jelly encloses the bottom of said container and at least partially lines the inner surface of said container;

(b) encapsulating said active principle with additional petroleum jelly;

(c) introducing said container containing said active principle(s) and said petroleum jelly into a mixer, said container having a perforated plug connected to the top of said container, and said mixer containing at least one excipient in heated liquid state; and (d) melting said petroleum jelly by immersion of said container within said at least one excipient being in a heated liquid state and thence diffusing and microdosing said active principle(s) therein.

2. The method as defined by claim 1, said weighing being carried out in a fume cupboard with vertical laminar flow or in a sealed enclosure, to avoid risk of contamination with a toxic active principle.

3. The method as defined by claim 1, said container having frustoconical dimensions.

4. The method as defined by claim 1, said petroleum jelly having a viscosity ranging from 130,000 and 550,000 Cps.

5. The method as defined by claim 1, said petroleum jelly permitting maximal limitation of the paraffin oil exudation phenomena.

6. The method as defined by claim 1, said active principle(s) comprising calcitriol.

7. The method as defined by claim 1, said at least one excipient comprising a mixture of white petroleum jelly and paraffin.

8. The method as defined by claim 7, said at least one excipient comprising a mixture of from 50% to 60% white petroleum jelly and from 40% to 50% paraffin.

9. The method as defined by claim 1, said step (d) comprising rotating said receptacle within said at least one excipient in heated liquid state.

10. The method as defined by claim 1, said step (d) comprising constantly diffusing and microdosing said active principle(s) within said at least one excipient in heated liquid state.

11. The method as defined by claim 6, the calcitriol being at a final concentration of 3 ppm.

* * * * *